United States Patent [19]

Dulka et al.

[11] Patent Number: 4,627,006

[45] Date of Patent: Dec. 2, 1986

[54] METHOD FOR DETERMINING THE RADIATION THRESHOLD OF NON-METALLIC MATERIALS

[75] Inventors: Catherine P. Dulka, West Chester; Evan H. Komito, King of Prussia, both of Pa.

[73] Assignee: General Electric Company, San Jose, Calif.

[21] Appl. No.: 682,952

[22] Filed: Dec. 18, 1984

[51] Int. Cl.$^4$ ........................ G06F 15/52; G01T 1/167
[52] U.S. Cl. ..................................... 364/527; 364/550
[58] Field of Search ............................. 364/527, 550; 250/338 R, 341

[56] References Cited

U.S. PATENT DOCUMENTS 3,524,983  8/1970  Voelz .................................. 250/341

OTHER PUBLICATIONS

*Calculation of Thermogravimetric Data by Electronic Digital Computer*, J. R. Soulen, Analytical Chemistry, vol. 34, No. 1, Jan. 1962, p. 136.
*Use of the Computer to Calculate Thermodynamic Constants from Thermogravimetric Curves*, J. Schempf et al., Pennsylvania State University, Analytical Chemistry, vol. 38, No. 3, Mar. 1966, p. 520.
*The Effect of Nuclear Radiation on the Mechanical, Weight Loss, and Electrical Properties of Sterling Resins, Varnishes and Compounds*, G. B. Fleeson, Sterling Technical Report presented at the Electrical/Electronics Insulation Conference in Chicago, Illinois, in Oct. of 1983.

*Primary Examiner*—L. T. Hix
*Assistant Examiner*—Douglas S. Lee
*Attorney, Agent, or Firm*—Ivor J. James, Jr.; Raymond G. Simkins

[57] ABSTRACT

An improved method for determining the nuclear radiation threshold of a non-metallic material with the aid of a computer is disclosed, in which differently irradiated samples of the material are subjected to thermogravimetric analysis. From the resultant pyrolytic weight-loss, temperature and elapsed time data, the reaction rates are determined for different orders of reaction values and are plotted against inverse temperature values to obtain the activation energy corresponding to each sample. By plotting activation energy against radiation dose for each sample, the radiation threshold of the material is obtained.

4 Claims, 5 Drawing Figures

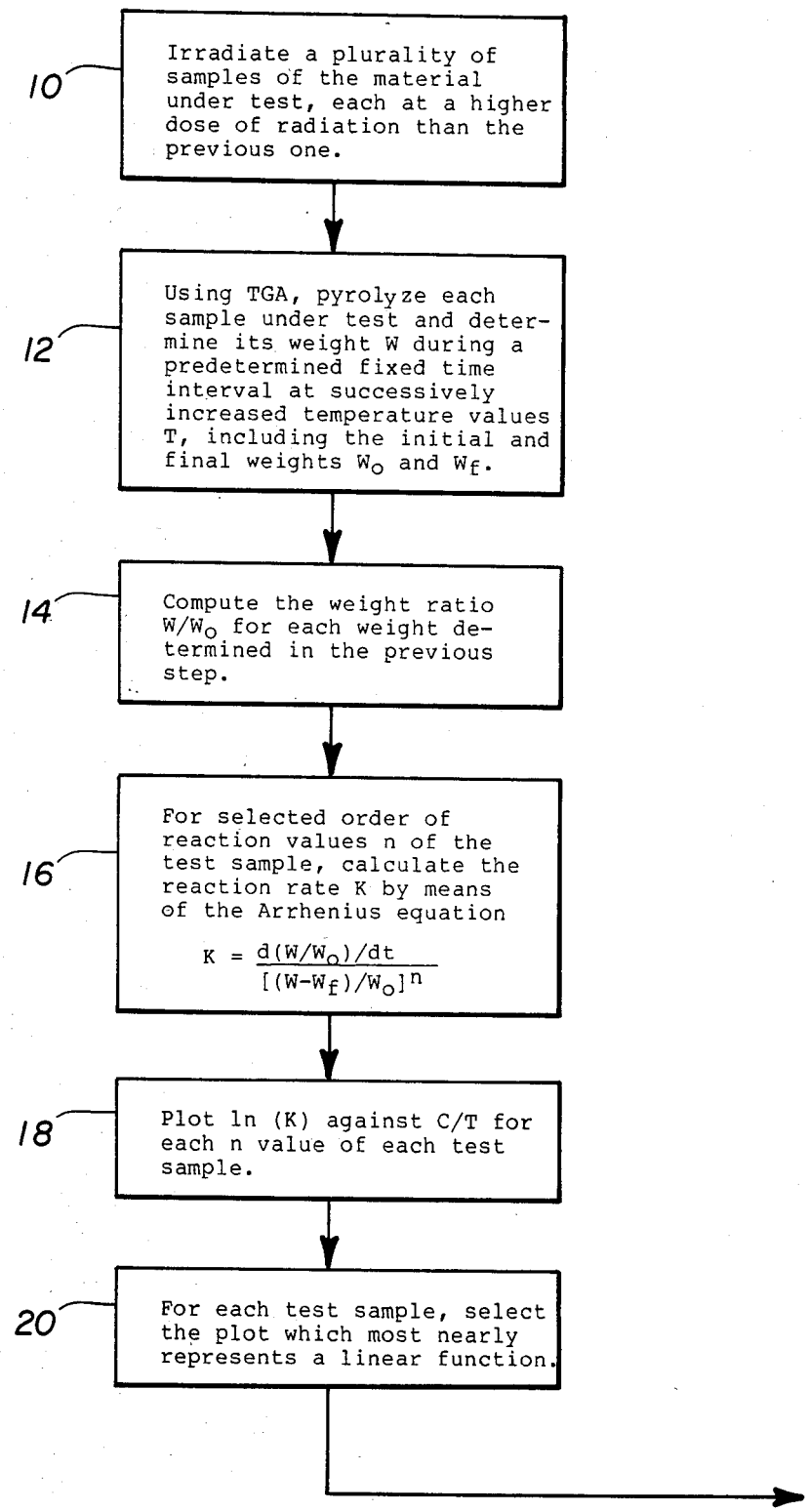

METHOD FOR DETERMINING THE RADIATION THRESHOLD OF NON-METALLIC MATERIALS

The present invention relates in general to the determination of the nuclear radiation threshold of different materials, and more particularly to a method for determining the radiation threshold of non-metallic materials by the use of thermogravimetric analysis.

BACKGROUND OF THE INVENTION

Certain types of equipment used in nuclear power plants, such as switch gear motors and relays, or portions thereof, may be made from synthetic molded materials like phenolics, to which mineral or organic fillers, such as wood flour, have been added. In order to insure the integrity of nuclear reactor facilities, it is frequently necessary to know the level of radiation which will cause the electrical and/or mechanical properties of such materials to begin to deteriorate, hereinafter referred to as the radiation threshold of the material. For example, it may be necessary to know the radiation level which will begin to produce a reduction of the thermal insulation properties of the material, or a reduction in tensile strength.

In accordance with conventional techniques, radiation resistance is generally measured as a function of the deterioration from the norm of the desired properties of the material under test. Typically, samples of the material are irradiated and then subjected to physical tests. Such measurements are complicated and time consuming, and they usually require a large number of specially machined samples of the material under test. Further, a number of these tests, such as the determination of the rupture strength of the material, require samples of relatively large size which are difficult to position inside a radiation chamber for the purpose of a test. As such, the cost of such tests is often high.

OBJECTS OF THE INVENTION

It is a principal object of the present invention to provide a new and rapid method for determining the radiation threshold of non-metallic materials, which is not subject to the foregoing problems and disadvantages.

It is another object of the invention to provide a simple method of radiation threshold determination for non-metallic materials which only requires samples of relatively small size.

It is still another object of the invention to provide a method of radiation threshold determination for non-metallic materials which does not require specially machined samples and which is less costly than conventional methods presently being used.

SUMMARY OF THE INVENTION

In accordance with the foregoing objects, the present invention is directed to a new and improved method for determining the radiation threshold of non-metallic materials. Samples that have been subjected to different doses of radiation are pyrolyzed while undergoing thermogravimetric analysis. Weight loss is recorded as a function of temperature increase. Using a computer, the Arrhenius equation is used to determine the pyrolytic reaction rate as a function of temperature. The different values obtained for the reaction rates are then plotted against the inverse values of the corresponding reaction temperatures. The resultant curve permits further evaluation of the Arrhenius pre-exponential constant and activation energies for the pyrolytic reaction under consideration. Activation energy values for the differently irradiated samples of the material under test are then plotted against radiation dose values. The plot so obtained indicates the radiation threshold of the material.

These and other objects of the invention, together with further features and advantages thereof, will become apparent from the following detailed specification when read in conjuction with the accompanying drawings.

BRIEF DESCRIPTION OF THE DRAWINGS

FIGS. 1A and 1B outline the steps of a preferred embodiment of the present invention in flow chart form.

DESCRIPTION OF THE INVENTION

In accordance with the present invention, the material to be tested may be a phenolic polymer material, and small samples of it, on the order of milligram quantities, are selected for pyrolytic thermal analysis. In a preferred embodiment of the invention, this analysis is performed thermogravimetrically, sometimes referred to herein as TGA.

Figure 1B:
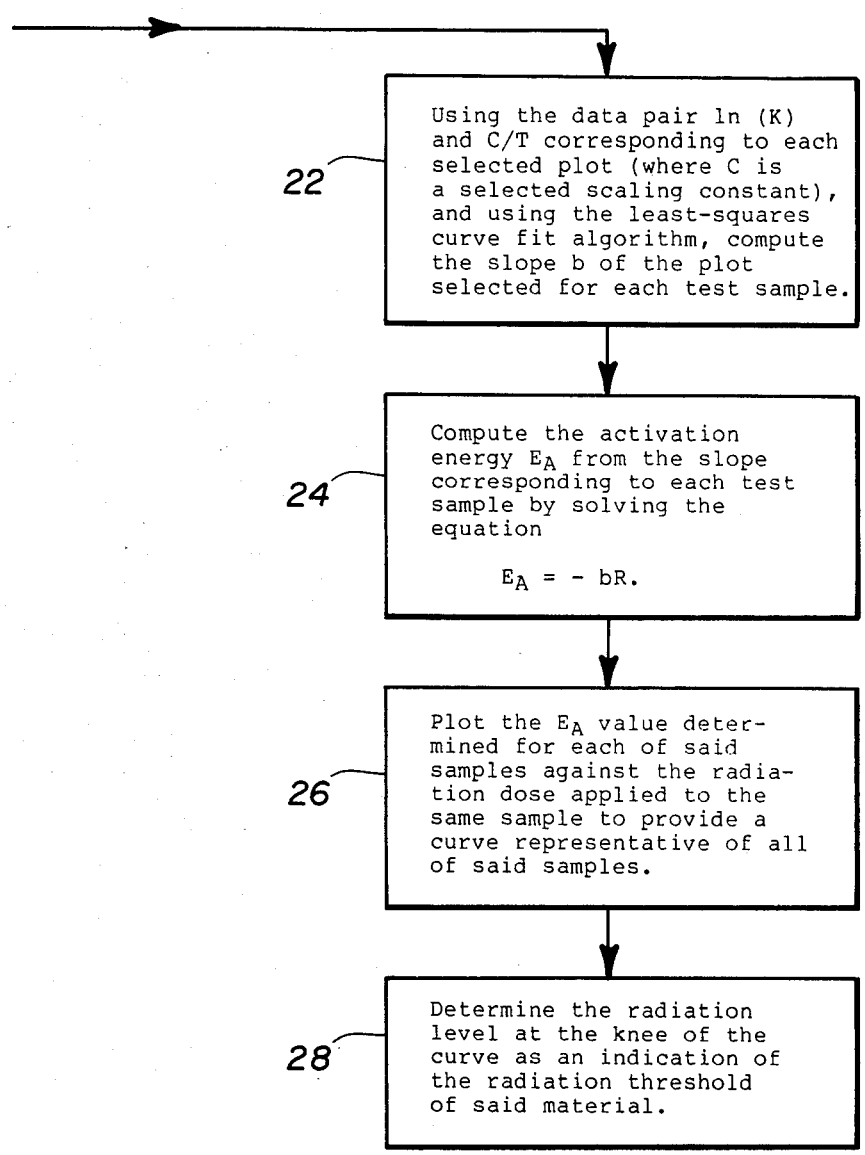

In FIGS. 1A and 1B the steps of a preferred embodiment of the invention are illustrated in flow chart form. It is intended that the computations required by the method herein be performed by a computer, e.g. a machine commercially available under the name Honeywell DPS 8/70, which is programmed to carry out the subroutines by which the method outlined in FIGS. 1A and 1B is implemented. These subroutines are set forth in Appendix A, which is part of this specification. It will be clear to those skilled in the art that the invention is not limited to the use of the above-referenced computer, and that it may be implemented in different ways.

As shown in block 10 of FIG. 1, each sample is irradiated at a different radiation exposure level, for example, 10K, 100K, 1M, 10M, and 100M rads. Another set of samples remains unirradiated and provides a base line value for comparison. As set forth in block 12, the irradiated samples are individually subjected to thermal analysis through pyrolysis, which is preferably carried out in a thermogravimetric analyzer furnace. The unirradiated samples will also be subjected to this procedure. TGA techniques are well known in the field of thermochemistry, as shown for example in U.S. Pat. Nos. 3,271,996 and 3,902,354. As each sample is pyrolyzed in the TGA furnace during a predetermined fixed time interval at successively increased temperature values, a recorder records the weight W of the decomposing substance as a function of elapsed time and temperature, throughout fixed time and temperature intervals.

The first series of steps in the preferred method of the present invention is set forth in Subroutine No. 1 in Appendix A, and it includes three functions. First, it stores data pairs, each consisting of a temperature value T (originally in °C., later converted to °K.) and the weight ratio $W/W_o$ determined for that temperature, where $W_o$ is the initial weight of the sample, and W is the remaining weight of the sample at time t. These values may be manually or automatically inserted into the computer as they are derived from the ongoing analysis. The above steps are further illustrated in blocks 12 and 14 of FIG. 1.

Figure 2:
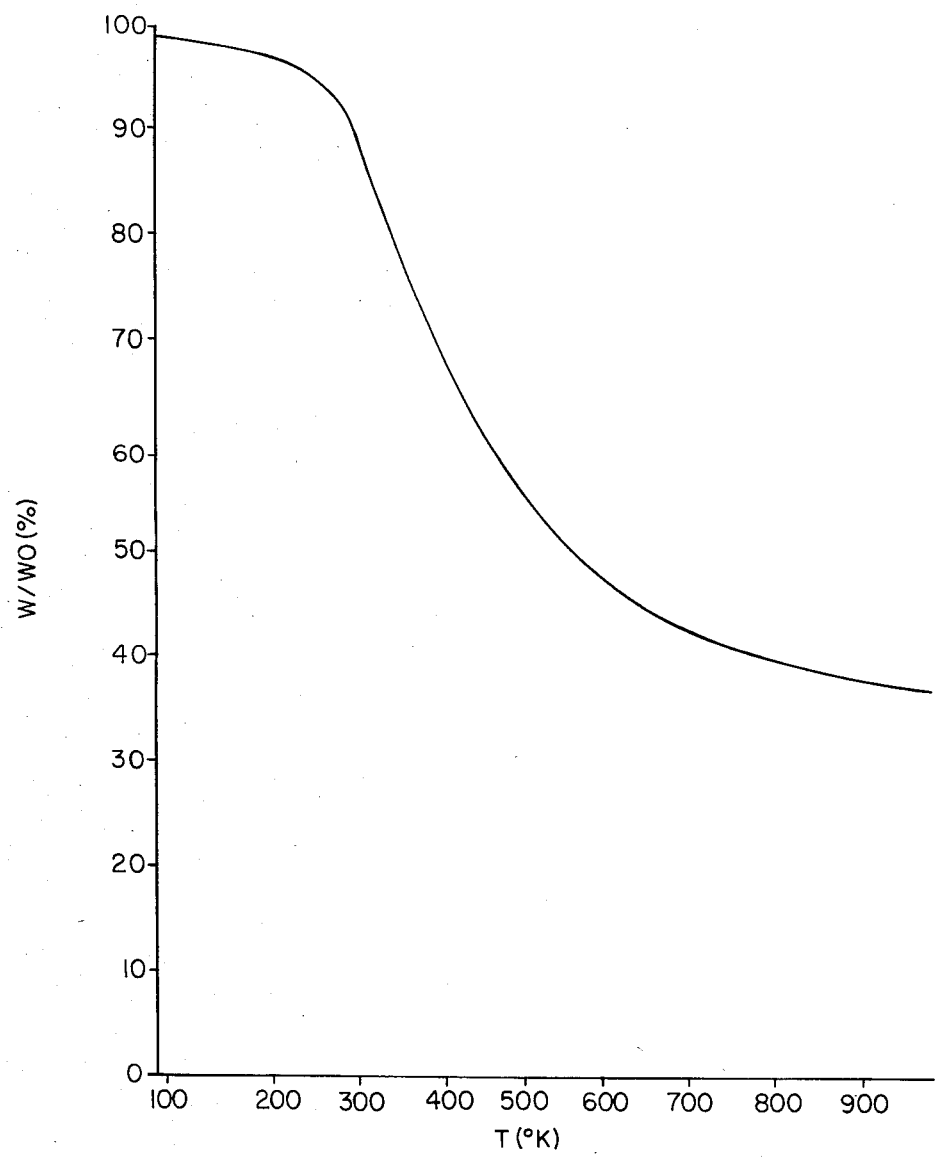
FIG. 2 is a plot of weight ratio of an exemplary test sample as a function of temperature.

For each test sample, the data required to plot a graph of the weight ratio as a function of temperature T is computed. If desired, the data may be computer plotted to provide a graph as shown in FIG. 2. The graph represents the particular decomposition characteristics of the test sample.

The next function of Subroutine No. 1 is illustrated in blocks 16 and 18 and involves the determination of the reaction rate K and the plotting of K. K can be expressed in terms of two Arrhenius-type equations:

$$K = \frac{d(W/W_o)/dt}{[(W - W_f)/W_o]^n} \quad (1)$$

$$K = Z \exp(-E_A/RT) \quad (2)$$

where
- $W_f$ = fiinal weight of sample after decomposition;
- n = order of the pyrolytic reaction;
- Z = collision frequency, i.e. the pre-exponential factor;
- $E_A$ = activation energy;
- R = Universal gas constant; and
- T = temperature in °K.

The computer is programmed to provide multiple values of K for each sample because the value of the of the order of reaction n is not usually known in advance. Therefore, K is preferably determined for at least three trial values of n, for example where n is 1, 2 and 3, respectively.

Figure 3:
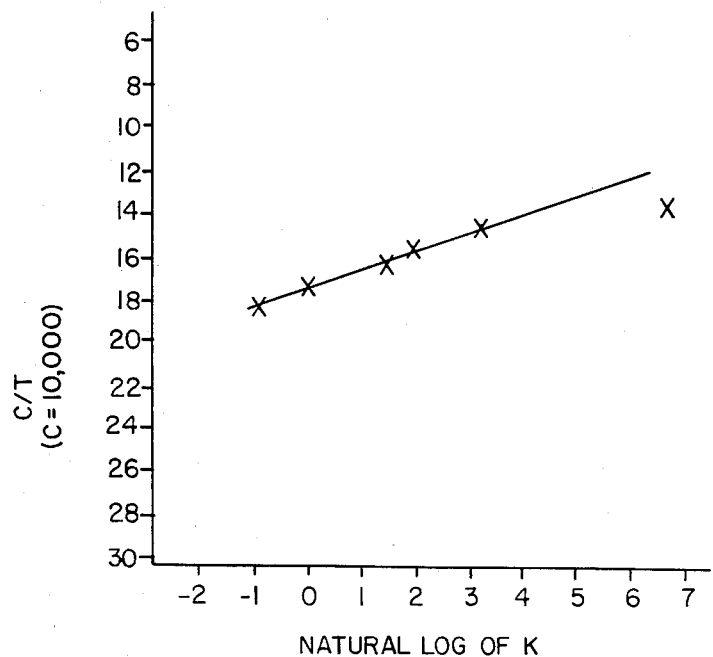
FIG. 3 is a plot of pyrolytic reaction rate as a function of inverse temperature values for an exemplary test sample.

As shown in block 18 of FIG. 1, and in Subroutine No. 2 of Appendix A, each value of K is plotted by the computer against a corresponding value for the inverse of the temperature T, multiplied by a scaling constant C. C is selected equal to or greater than $10^4$ so that whole number values can be plotted, rather than decimal values. Such a plot is illustrated in FIG. 3 for n=3.

In the prefered embodiment of the invention, the activation energy $E_A$ is determined as follows: $E_A$ is proportional to the slope of the straightest line obtained when plotting the natural logarithm of the pyrolytic reaction rate against the inverse (C/T) of the temperature T for that pyrolytic reaction. In the prefered embodiment, as shown beginning with block 20 in FIG. 1, the plots of ln (K) against C/T for the different values of n of a given test sample are visually inspected to determine and select the plot of the test sample which exhibits the straightest line, i.e. which most nearly represents in linear function. The selection process is carried out for each test sample. The plots so selected are defined by coordinate data pairs of values for ln (K) and C/T, i.e. every value of C/T has a corresponding value of ln (K) determined by the corresponding remaining weight fraction $W/W_o$.

To determine the slope b of the selected plot, a "least-squares curve fit" of this data is preformed with the aid of the computer, as set forth in block 22 of FIG. 1B. The method of least-squares is a well-known mathematical technique and is commonly used to solve the problem of fitting a theoretical straight line to a set of experimentally observed points, here the set of points representing coordinate values of ln (K) and C/T, for each test sample. Examples of the application of the least-squares method can be found in *Calculus and Analytic Geometry*, Thomas, Jr., alt. ed., Addison-Wesley Publishing Company, Inc., 1972, pp. 716–720.

Equation 2, stated previously as $$K = Z \exp(-E_A/RT),$$

is manipulated into a form which is amendable to the application of the least-squares method. The detailed steps involved are shown in Subroutine No. 3 of Appendix A. Since the slope b is proportional to $E_A$, the activation energy $E_A$ is then computed from b as shown in block 24 of FIG. 1B.

An alternative method for determining $E_A$ follows the above sequence of steps through FIG. 1, block 18. Thereafter, the least-squares curve fit algorithm is performed on the set of data pairs for each value of n. Each n value results in a different value of K, and in a different curve of ln (K) against C/T. As shown in Subroutine No. 3 in Appendix A, for every value of $E_A$ calculated, there is also calculated a standard deviation value $\hat{\sigma}_e$ (EST STD DEV). This deviation is an indicator of the "goodness-of-fit" of the theoretical straight line curve to the set of data coordinates for ln (K) and C/T. When the plots of ln (K) against C/T for each value of n are too similar for visual discrimination, $\hat{\sigma}_e$ values are compared instead. For each test sample, the plot having the smallest $\hat{\sigma}_e$ value necessarily is the plot which most nearly represents a linear function. The calculated $E_A$ value corresponding to that plot is selected as the appropriate $E_A$ value for that particular sample.

Figure 4:
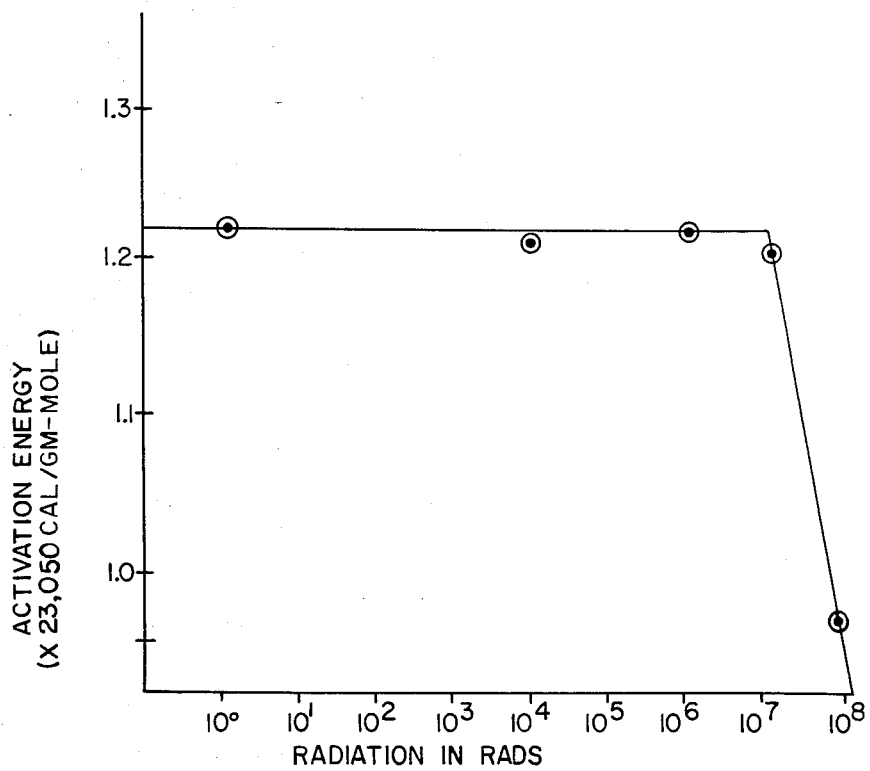
FIG. 4 is a plot of the radiation dose applied to each of a plurality of exemplary test samples against the corresponding activation energy.

Following the computation of $E_A$ for each test sample, each $E_A$ value is plotted against the corresponding radiation dose applied to that test sample, as set forth in block 26 of FIG. 1B. The resultant curve is shown in FIG. 4, depicting activation energy $E_A$ as a function of increasing radiation level. As shown in FIG. 4, the curve displays a knee at approximately $10^7$ rads for the phenolic material in the example under consideration. As set forth in block 28, this value represents the radiation threshold for the material under test.

It will be clear from the foregoing discussion of a preferred embodiment of the invention that many other materials can be tested by this method, for example varnishes, polyesters, and acrylics. In addition to determining the radiation threshold of materials, the invention may also find application in determining how radiation exposure affects the thermochemical characteristics of many kinetic reactions by the study of the activation energies of those reactions.

While the invention herein has been described with reference to specific embodiments thereof, it is to be understood that the invention is not so limited and that numerous changes, variations, substitutions, and equivalents, in full or in part, will now occur to those skilled in the art without departing from the spirit and scope of the invention. Accordingly, it is intended that the invention be limited only by the scope of the appended claims.

APPENDIX A

Subroutine No. 1

```
10 PRINT "Reaction Rate Comp + Plots + n, Z, & EA Comp"
20 PRINT "ENTER WF/WO, TEMP RATE (DEG-C/MIN), & NO. OF
   DATA POINTS"
30 INPUT F1, R, S
40 DIM T(100), W(100), A(100), B(100), C(100), D(100),
   E(100), K(100)
50 PRINT "INPUT S DATA PAIRS OF TEMP (DEG-C) AND W/WO"
60 PRINT "IN FORMAT: T(N), W(N)"
70 FOR N = 1 TO S
80 INPUT T(N), W(N)
90   T(N) = T(N) + 273                          °K = °C + 273
100 NEXT N
110 PRINT "ENTER REACTION ORDER, OR 999 TO STOP"
120 INPUT L
130 IF L = 999 THEN 1020
140 FOR N = 2 TO (S-1)
150 LET A(N) = W(N-1) - W(N+1)                  Δ(W/W₀)
160 LET B(N) = T(N+1) - T(N-1)                  ΔT
170 LET C(N) = A(N)/B(N)                        ≈ ∂(W/W₀)∂T
180 LET D(N) = W(N) - F1                        (W-Wf)/W₀
190 LET E(N) = D(N)↑L                           [(W-Wf)/W₀]^L
200 LET K(N) = C(N)*R/E(N)                      K = ∂(W/W₀)/∂T*dT/dt
                                                    ─────────────────
                                                    [(W-Wf)/W₀]^L
210 NEXT N
220 PRINT
230 PRINT "FOR REACTION ORDER ="; L
240 PRINT
250 PRINT "   T=KELVIN","    1/T","    K-1/MIN","     LN(K)"
260 FOR N = 2 TO (S-1)
270 PRINT USING 280, T(N), 1/T(N), K(N), LOG(K(N))
280:         ####     .######    #.####↑↑↑↑       ###.####
290 NEXT N
300 RESTORE
310 PRINT
```

Line 150: $\Delta(W/W_0)$
Line 160: $\Delta T$
Line 170: $\approx \partial(W/W_0)\partial T$
Line 180: $(W-W_f)/W_0$
Line 190: $[(W-W_f)/W_0]^L$
Line 200: $K = \dfrac{\partial(W/W_0)/\partial T \cdot dT/dt}{[(W-W_f)/W_0]^L}$

Subroutine No. 2

```
320 REM    This subroutine plots ln(K) vs 1/T.
330 DIM F(100)
340 FOR N = 2 TO S-1
350    F(N) = INT((1E4/T(N)) + .5)
360 NEXT N
370 PRINT"             NATURAL LOG OF K (1/MIN)"
380 PRINT USING 390
390:10000/T -8 -7 -6 -5 -4 -3 -2 -1 0 1 2 3 4 5 6 7
400 PRINT "(1/KELV) T  T  T  T  T  T  T  T  T  T  T  T  T  T  T  T
410 FOR G = 5 TO 30
420    A = 0
430    FOR N = 2 TO S-1
440       IF G <> F(N) THEN 490
450       PRINT G; TAB(9);">"; TAB(42+INT(4*LOG(K(N))+.5));"*"
460       A = 1
470       N = S-1
480       GO TO 490
490    NEXT N
500    IF A = 1 THEN 520
510       PRINT G; TAB(9);">"
520 NEXT G
530 PRINT
540 PRINT
```

Subroutine No. 3

```
550 REM    This subroutine performs a least-squares curve fit
560 REM    to evaluate the Arrhenius parameters n, Z, & E_A
570 I = 0
580 Y = 0
590 X = 0
600 J = 0
610 FOR N = 2 TO S-1
620    IF 10000/T(N) <= I THEN 660
630    J = J+1
640    Y = Y + LOG(K(N))                  Σln(K) ≡ Σy
```

```
650    X = X + 1/T(N)                    Σ(1/T) ≡ Σ x
660  NEXT N
670  Y = Y/J                             Σ ln(K)/n ≡ ȳ
680  X = X/J                             Σ(1/T)/n ≡ x̄
690  DIM G(100), H(100)
700  C = 0
710  D = 0
720  FOR N = 2 TO S-1
730    IF 10000/T(N) <= I THEN 780
740    G(N) = 1/T(N) - X                 x - x̄
750    H(N) = LOG(K(N)) - Y              y - ȳ
760    C = G(N) * H(N) + C               Σ(x-x̄)(y-ȳ)
770    D = G(N)↑2 + D                    Σ(x-x̄)²
780  NEXT N
790  B = C/D                             B=Σ(x-x̄)(y-ȳ)/Σ(x-x̄)²=$E_A$/R
800  A = Y - B*X                         A=ȳ-Bx̄ ~ "0"-intercept of ln(K)
810  F = 0
820  FOR N = 2 TO S-1
830    IF 10000/T(N)<= I THEN 860
840    E = A + B/T(N)                    ŷ = A + Bx
850    F = F + (LOG(K(N)) - E)↑2         Σ(y-ŷ)²
860  NEXT N
870  H1 = SQR(F/(J-2))                   H1≡ σ̂_e = Σ(y-ŷ)²/(n-2)~± ln(K)
880  H = EXP(H1)/60                      H ≡ σ̂_e ~ ±K
890  Z = EXP(A)/60
900  E1 = -1.987*B                       $E_A$ = R·$E_A$/R ~ Cal/gm-mole
910  E2 = E1*1.8                         $E_A$ ~ Btu/lb-mole
920  PRINT
930  PRINT
940  PRINT USING 950
950: REACTION   COLLISION    ACTIVATION ENERGY    DATA SCATTER
960  PRINT USING 970
970:    ORDER FREQ-1/SEC CAL/GM-MOLE BTU/LB-MOLE (EST STD DEV)
980  PRINT USING 990, L, Z, E1, E2, H
990:    #    #.####↑↑↑↑     #.####↑↑↑↑     #.####↑↑↑↑     #.##↑↑↑↑
1000 PRINT
1010 GO TO 110
1020 END
```

What is claimed is:

1. A method of determining the radiation threshold of a non-metallic material with the aid of a computer, comprising the steps of:
   subjecting each of a plurality of samples of said material to a different dose of radiation;
   pyrolyzing each sample;
   computing the activation energy $E_A$ for each of said samples;
   plotting a graph of said calculated $E_A$ values for all of said samples against the corresponding radiation doses applied to said samples; and
   determining the radiation level at the knee of said curve as representative of the radiation threshold of said material.

2. A method of determining the radiation threshold of a non-metallic material, comprising the steps of:
   (A) irradiating a plurality of samples of said material such that successive samples receive different doses of radiation;
   (B) subjecting said samples to thermogravimetric analysis, including performing on each sample under test the operations of:
      (1) determining the weight W of said test sample during a predetermined time interval at successively increasing temperature values T, including the initial and final weights $W_o$ and $W_f$ respectively, said temperature values being selected from a range of temperatures which includes the pyrolytic reaction temperature range of said material;
      (2) calculating the weight ratio $W/W_o$ for each weight determined;
      (3) determining the rate of reaction K in accordance with the equation $$K = \frac{d(W/W_o)/dt}{[(W - W_f)/W_o]^n}$$

for selected values of n, where
   n = the order of said reaction;
   (C) for each of said values of n, plotting ln (K) against C/T, where C is a selected scaling constant;
   (D) from the plots provided in step (C) for said test sample, selecting the plot which most nearly represents a linear function;
   (E) determining the slope of said selected plot, said slope being representative of the activation energy $E_A$ of said test sample;
   (F) plotting the $E_A$ value determined for each of said samples against the radiation dose applied to the same sample to provide a curve representative of all of said samples; and
   (G) determining the radiation level at the knee of said curve as an indication of the radiation threshold of said material.

3. A method of determining the radiation threshold of a non-metallic material with the aid of a computer, comprising the steps of:
   (A) irradiating a plurality of samples of said material such that successive samples receive increased doses of radiation;
   (B) subjecting said samples to thermogravimetric analysis, including performing on each sample under test the operations of:
      (1) determining the weight W of said test sample during a predetermined time interval at successively increased temperature values T, including the initial and final weights $W_o$ and $W_f$ respectively, said temperature values being selected from a range of temperatures which includes the pyrolytic reaction temperature range of said material;
      (2) computing the weight ratio $W/W_o$ for each weight determined;
      (3) storing the cumulative time t elapsed to reach each of said temperature values, and storing discrete data pairs, each consisting of one of said temperature values and its corresponding weight ratio;
      (4) for each weight ratio stored, solving the Arrhenius equation in said computer $$K = \frac{d(W/W_o)/dt}{[(W - W_f)/W_o]^n}$$

for selected values of n, where
   K = the rate of said pyrolytic reaction, and
   n = the order of said reaction;
   (C) for each of said selected values of n corresponding to said test sample, computer-plotting ln (K) against C/T, where C is a selected scaling constant;
   (D) from the plots provided by step (C) for said test sample, selecting the plot which most nearly represents a linear function;
   (E) computing the slope b of said selected plot for said test sample by performing the least-squares curve fit algorithm thereon;
   (F) computing the activation energy $E_A$ for said test sample by solving the equation $$E_A = -bR$$

where
   R = the universal gas constant;
   (G) plotting the $E_A$ value determined for each of said samples against the radiation dose applied to the same sample to provide a curve representative of all of said samples; and
   (H) determining the radiation level at the knee of said curve as an indication of the radiation threshold of said material.

4. A method of determining the radiation threshold of a non-metallic material with the aid of a computer, comprising the steps of:
   (A) Irradiating a plurality of samples of said material such that the dosage received by successive samples increases in steps;
   (B) subjecting said samples to thermogravimetric analysis, including performing on each sample under test the operations of:
      (1) determining the weight W of said test sample during a predetermined time interval at successively increased temperature values T, including the initial and final weights $W_o$ and $W_f$ respectively, said temperature values being selected from a range of temperatures which includes the pyrolytic reaction temperature range of said material;
      (2) computing the weight ratio $W/W_o$ for each weight determined;
      (3) storing the cumulative time t elapsed to reach each of said temperature values, and storing discrete data pairs each consisting of one of said temperature values and its corresponding weight ratio;

(4) for each weight ratio stored, solving the Arrhenius equation in said computer $$K = \frac{d(W/W_o)dt}{[(W - W_f)/W_o]^n}$$

for selected values of n, where
K = the rate of said pyrolytic reaction, and
n = the order of said reaction;

(C) for each of said selected values of n corresponding to said test sample, computer-plotting ln (K) against C/T,
where C is a selected scaling constant;

(D) performing the least-squares curve fit algorithm on each of the plots obtained in step (C) to obtain a slope and an estimated standard deviation value for each plot of said test sample;

(E) selecting the slope b for each of said samples which corresponds to the smallest standard deviation value;

(F) computing the activation energy $E_A$ for said test sample by solving the equation $$E_A = -b\,R$$

where
R = the universal gas constant;

(G) plotting the $E_A$ value determined for each of said samples against the radiation dose applied to the same sample to provide a curve representative of all of said samples; and (H) determining the radiation level at the knee of said curve as an indication of the radiation threshold of said material.

* * * * *